United States Patent
Schulz et al.

(10) Patent No.: US 9,072,916 B2
(45) Date of Patent: *Jul. 7, 2015

(54) AQUEOUS ANTI-PERSPIRATION FORMULATION

(75) Inventors: Ulrike Schulz, Hamburg (DE); Lara Terstegen, Hamburg (DE); Torben Zwiener, Hamburg (DE); Yvonne Eckhard, Hamburg (DE); Linda Engfeldt, Hamburg (DE); Heike Miertsch, Hamburg (DE); Thomas Nuebel, Hamburg (DE); Claudia Rohde, Tangstedt (DE); Michael Urban, Hamburg (DE); Gordon Christ, Frankfurt (DE); Katja Warnke, Hamburg (DE); Khiet Hien Diec, Hamburg (DE)

(73) Assignee: BEIERSDORF AG, Hamburg (DE)

( * ) Notice: Subject to any disclaimer, the term of this patent is extended or adjusted under 35 U.S.C. 154(b) by 132 days.

This patent is subject to a terminal disclaimer.

(21) Appl. No.: 10/574,219

(22) PCT Filed: Apr. 27, 2005

(86) PCT No.: PCT/EP2005/051894
§ 371 (c)(1),
(2), (4) Date: Oct. 3, 2006

(87) PCT Pub. No.: WO2005/105027
PCT Pub. Date: Nov. 10, 2005

(65) Prior Publication Data
US 2007/0218025 A1    Sep. 20, 2007

(30) Foreign Application Priority Data

Apr. 27, 2004  (DE) .................. 10 2004 020 711
Apr. 13, 2005  (DE) .................. 10 2005 017 032

(51) Int. Cl.
*A61K 8/26* (2006.01)
*A61Q 15/00* (2006.01)
*A61K 8/06* (2006.01)
*A61K 8/28* (2006.01)
*A61K 8/365* (2006.01)

(52) U.S. Cl.
CPC ........... *A61Q 15/00* (2013.01); *A61K 8/068* (2013.01); *A61K 8/26* (2013.01); *A61K 8/28* (2013.01); *A61K 8/365* (2013.01)

(58) Field of Classification Search
USPC ................... 424/65, 68, 400, 401
See application file for complete search history.

(56) References Cited

U.S. PATENT DOCUMENTS

| | | |
|---|---|---|
| 3,991,176 A | 11/1976 | Rubino |
| 4,078,050 A | 3/1978 | Hart |
| 4,089,942 A | 5/1978 | Boré et al. |
| 4,921,694 A | 5/1990 | Hoppe et al. |
| 5,318,778 A | 6/1994 | Schmucker et al. |
| 5,571,841 A | 11/1996 | Yu et al. |
| 5,648,067 A | 7/1997 | Dillenburg et al. |
| 5,652,266 A | 7/1997 | Bobier-Rival et al. |
| 5,718,888 A | 2/1998 | Klier et al. |
| 5,863,525 A | 1/1999 | Angelone, Jr. et al. |
| 5,925,338 A | 7/1999 | Karassik et al. |
| 6,007,799 A | 12/1999 | Lee et al. |
| 6,042,816 A * | 3/2000 | Shen .............................. 424/65 |
| 6,156,296 A | 12/2000 | Riedel et al. |
| 6,245,325 B1 | 6/2001 | Shen |
| 6,468,551 B1 | 10/2002 | Diec et al. |
| 6,585,983 B1 | 7/2003 | Gers-Barlag et al. |
| 6,607,733 B1 | 8/2003 | Diec et al. |
| 6,911,210 B1 | 6/2005 | Bormann et al. |
| 6,942,871 B2 | 9/2005 | Bruning et al. |
| 6,989,151 B2 | 1/2006 | Gers-Barlag et al. |
| 7,189,406 B1 | 3/2007 | Gross |
| 7,294,330 B2 * | 11/2007 | Banowski et al. ............. 424/65 |
| 2002/0077372 A1 * | 6/2002 | Gers-Barlag et al. ........... 516/98 |
| 2003/0175221 A1 | 9/2003 | Gers-Barlag et al. |
| 2005/0265940 A1 * | 12/2005 | Okada ............................ 424/66 |

FOREIGN PATENT DOCUMENTS

| | | |
|---|---|---|
| AU | 93/49509 | 3/1994 |
| DE | 2703642 | 8/1977 |
| DE | 3740186 | 1/1989 |
| DE | 3938140 | 8/1991 |
| DE | 4009347 | 9/1991 |
| DE | 4204321 | 8/1993 |
| DE | 4229707 | 3/1994 |
| DE | 4229737 | 3/1994 |
| DE | 4237081 | 5/1994 |
| DE | 4309372 | 9/1994 |
| DE | 4324219 | 1/1995 |
| DE | 69523805 | 10/1995 |
| DE | 4423450 | 1/1996 |

(Continued)

OTHER PUBLICATIONS

English Language Abstract of DE 199 62 881.
English Language Abstract of DE 102 37 054.
English Language Abstract of DE 44 23 450.
English Language Abstract of DE 198 44 261.
English Language Abstract of DE 196 02 111.
English Language Abstract of DE 101 07 628.
English Language Abstract of EP 0 775 486.
English Language Abstract of DE 102 10 461.

(Continued)

*Primary Examiner* — Sue Liu
*Assistant Examiner* — Luke Karpinski
(74) *Attorney, Agent, or Firm* — Abel Law Group, LLP

(57) ABSTRACT

The invention relates to a cosmetic formulation with improved effectiveness and reduced stickiness, comprising at least one activated aluminum antiperspirant active ingredient, at least one alpha-hydroxycarboxylic acid and water.

29 Claims, No Drawings

(56) References Cited

FOREIGN PATENT DOCUMENTS

| | | |
|---|---|---|
| DE | 19509079 | 9/1996 |
| DE | 19602111 | 7/1997 |
| DE | 19608775 | 9/1997 |
| DE | 19842787 | 3/2000 |
| DE | 19844261 | 3/2000 |
| DE | 19919481 | 11/2000 |
| DE | 19962881 | 6/2001 |
| DE | 10107628 | 8/2002 |
| DE | 10210461 | 9/2003 |
| DE | 10237054 | 2/2004 |
| EP | 0775486 | 5/1997 |
| EP | 0925783 | 6/1999 |
| WO | 92/05767 | 4/1992 |
| WO | 94/12115 | 6/1994 |
| WO | 96/28132 | 9/1996 |
| WO | 97/06777 | 2/1997 |
| WO | 98/15255 | 4/1998 |
| WO | 98/32418 | 7/1998 |
| WO | WO03039505 A3 * | 5/2003 |

OTHER PUBLICATIONS

English Language Abstract of DE 42 04 321.

English Language Abstract of EP 0 925 783.

English Language Abstract of DE 40 09 347.

U.S. Appl. No. 10/574,231 entitled "Transparent Cosmetic or Dermatological Formulation".

U.S. Appl. No. 11/586,585 entitled "Optically Appealing Cosmetic or Dermatological Preparation".

U.S. Appl. No. 10/574,230 entitled "Transparent Cosmetic Microemulsion-Based Formulation Containing an Alpha-Hydroxycarboxylic Acid".

A. Rosenberg, "Antiperspirant Technology", SÖFW-Journal, vol. 128, No. 4, pp. 16-18 (2002).

* cited by examiner

AQUEOUS ANTI-PERSPIRATION FORMULATION

CROSS-REFERENCE TO RELATED APPLICATIONS

The present application is a U.S. National Stage of International Application No. PCT/EP2005/051894, filed Apr. 27, 2005, which claims priority of German Patent Application No. 10 2004 020 711.9, filed Apr. 27, 2004, and German Patent Application No. 10 2005 017 032.3, filed Apr. 13, 2005.

BACKGROUND OF THE INVENTION

1. Field of the Invention

The invention relates to an aqueous cosmetic antiperspirant formulation with increased antiperspirant effectiveness.

For aesthetic reasons in particular, transparent and translucent products are preferred by many consumers. Thus, transparent formulations are often used, for example, as deodorant or antiperspirant (AP). These can nowadays be realized by the following technologies:

1. aqueous-alcoholic formulations
2. water-in-silicone emulsions
3. microemulsions The aqueous-alcoholic deodorant and AP formulations are mostly based on water and alcohol as medium, deodorant and antiperspirant agents as active ingredients, and also perfume, solubilizers and thickeners (mostly based on carbohydrate) as additional agents. They are perceived by the consumer as being fresh and cooling, but are at the same time encumbered with a whole series of disadvantages. Thus, for example, application primarily to freshly shaved skin is associated with incompatibilities as a result of the alcohol content. Another major disadvantage is the fact that relatively large amounts of oil cannot be incorporated into such systems. As a result of the high content of antiperspirant salt required for highly effective performance, a white residue remains following application to the skin; this is perceived by the consumer as being extremely troublesome. However, due to the absence of a sufficiently large oil phase for technical reasons, this cannot be concealed. Moreover, the use of carbohydrate thickeners leads to high stickiness of the product after the alcohol has evaporated.

Water-in-silicone emulsions belong to the group of water-in-oil emulsions. The water phase comprising ethanol or polyhydric alcohols, such as, for example, propylene glycol and water-soluble active ingredients, such as AP agent and/or deodorant active ingredient, constitutes about 75-90% of the formulation. The oil phase consists of a volatile and a non-volatile silicone oil and also a silicone emulsifier.

2. Discussion of Background Information

The transparency of water-in-silicone emulsions is based on matching the refractive indices of the two phases. It is a drawback that even a difference in the indices of 0.0004 caused, for example, by evaporation, leads to cloudiness. WO 98/32418 and WO 92/05767 describe such deodorant or AP formulations based on W/Si emulsion.

One approach for solving the described disadvantages has been made possible through cosmetically pleasing alcohol-free and transparent products which are based on so-called microemulsions. These have the major advantage that even relatively large amounts of various oils—with all of the described positive effects for the consumer—can be stably incorporated. Formulations of this type are in principle available by means of phase inversion temperature technology (PIT) or high-pressure homogenization. The required stability of the emulsifier system to high concentrations of antiperspirant salts, however, places high demands on the formulation skill of the product developer.

WO 98/15255 describes microemulsions. However, a drawback even with these formulations is a sticky feel on the skin caused by the thickener, and the lack of a yield point.

It is an object of the present invention to provide a cosmetic preparation which enriches the prior art and helps to avoid its disadvantages.

In particular, it is the object of the present invention to provide a cosmetic formulation which is transparent and is characterized by minimized stickiness. In particular, the object was to provide an antiperspirant formulation which is transparent and has no cloudiness at all, which is characterized by a minimized stickiness and which has a defined yield point for optimized discharge and application.

To increase the antiperspirant effectiveness, it is customary to increase the amount of antiperspirant active ingredient, such as, for example, aluminum chlorohydrates ACH. Furthermore, so-called activated aluminum chlorohydrates (AACH) are known as antiperspirant active ingredients with increased effectiveness, e.g. EP 925783 or in the literature—Antiperspirants and Deodorants, 2nd Edition, Cosmetic and Technology Science, Vol. 20, 1999.

However, it is a problem here that the antiperspirant effectiveness is only possible to a limited degree through increasing the amount of active ingredient since, above a content of about 15% by weight of the AP active ingredient, saturation of the effectiveness is established and in addition disadvantages such as white residues and an unpleasant feel on the skin are increased.

A few chemical basics in this regard:

If aluminum salt $AlX_3$ of a strong acid (e.g. $AlCl_3$) is dissolved in water, then, in accordance with the reaction:

$$AlX_3 + 6H_2O \rightarrow Al(H_2O)_6^{3+} + 3X^-$$

the octahedrally constructed hexaaquaaluminum ion $[Al(H_2O)_6]^{3+}$ is formed, which acts as a weak cationic acid.

As a consequence of the acid effect, these are liable to hydrolysis and can be successively deprotonated as far as the hexahydroxoaluminate ion $[Al(OH)_6]^{3+}$.

Depending on the pH and the concentration of aluminum ions, three-dimensional structures are formed as a result of bridging with hydroxide ions and oxygen atoms. These processes, in which element atoms are bridged by hydroxide ions, are called olation and for bridges with oxide ions, the term used is oxolations.

Both reactions belong to the group of condensation reactions.

The polynuclear aluminum cations $[Al_m(OH)_n(H_2O)_o]^{p+}$ present in aqueous aluminum salt solutions belong to the group of isopolyoxo cations.

In order to achieve an increased antiperspirant effectiveness of classic aluminum chlorohydrate (ACH) solutions, these are thermally treated depending on concentration, temperature and pressure, and the resulting solutions are dried by means of spray-drying.

This leads to an increased amount of smaller molecule sizes being present in stable form. However, these activated aluminum complex salts (AACH) effective as antiperspirant disintegrate in water back to their original equilibrium state, meaning that in aqueous preparations increased effectiveness is lost.

Use of these activated ACH types (AACH) has therefore hitherto only made sense in nonaqueous systems since otherwise reconversion to the molecule size distribution as occurs in classic ACH solutions is possible, as described, for example, in the article by A. H. Rosenberg—Antitranspirant Technology, SÖFW-Journal, 128 (4) 2000.

It is therefore an object of the present invention to provide an aqueous preparation which has an increased antiperspirant effectiveness without the described disadvantages. In particular, it is therefore the object to provide aqueous cosmetic preparations which, despite the water content, have an increased antiperspirant effectiveness as a result of the addition of activated aluminum complex salts.

SUMMARY OF THE INVENTION

The present invention provides a cosmetic formulation comprising (a) at least one activated aluminum compound which is effective as antiperspirant, (b) at least one α-hydroxycarboxylic acid and (c) water.

In one aspect of the formulation, component (b) may comprise mandelic acid.

In another aspect, component (a) may comprise one or more activated aluminum salts. For example, component (a) may comprise activated aluminum chlorohydrate.

In still another aspect, the ratio of component (a) to component (b) may be from 15:1 to 1:1, e.g., from 12:1 to 2:1, or from 10:1 to 2.5:1.

In yet another aspect, the formulation of the present invention may comprise from 1% to 35% by weight, e.g., from 1% to 25% by weight, or from 1% to 20% by weight, of component (a), based on the total weight of the formulation.

In another aspect of the cosmetic formulation of the present invention, the formulation may comprise from 0.1% to 10% by weight, e.g., from 0.1% to 8% by weight, of component (b), based on the total weight of the formulation.

In another aspect, the cosmetic formulation of the present invention may comprise an O/W microemulsion such as, e.g., a microemulsion gel. For example, the formulation may comprise an oil-in-water microemulsion which comprises an oil phase, a water phase and less than 20% by weight of one or more emulsifiers, based on the total weight of the microemulsion. The oil phase may be essentially composed of constituents of low volatility.

The one more emulsifiers may comprise one or more O/W emulsifiers selected from polyethoxylated, polypropoxylated and polyethoxylated and polypropoxylated O/W emulsifiers and may further comprise one or more optional W/O emulsifiers.

The microemulsion may be obtainable by bringing a mixture comprising the water phase, the oil phase, the one or more O/W emulsifiers, the one or more optional W/O emulsifiers and one or more other optional components selected from auxiliaries, additives and active ingredients to a temperature within or above the phase inversion temperature range and subsequently cooling the mixture to room temperature.

The droplets of the discontinuous oil phase of the microemulsion may be joined together by one or more crosslinker substances whose molecules comprise at least one hydrophilic region which has a size suitable for bridging the distance between the droplets and at least one hydrophobic region which is able to enter into hydrophobic interaction with the droplets.

In yet another aspect, the cosmetic formulation of the present invention may have a defined yield point, for example, a yield point of from 40 to 120 Pa, determined at 25° C. by means of a shear stress time ramp of 40 Pa/min.

In a still further aspect, the formulation may be suitable for application to the human skin.

The present invention also provides a cosmetic formulation which comprises (a) activated aluminium chlorohydrate, (b) mandelic acid and (c) water.

In one aspect of the formulation, the ratio of component (a) to component (b) may be from 10:1 to 2.5:1.

In another aspect, the formulation may comprise from 1% to 20% by weight of component (a) and from 0.1% to 8% by weight of component (b), each based on the total weight of the formulation.

In yet another aspect, the formulation may comprise an O/W microemulsion.

The present invention also provides an antiperspirant product which comprises the cosmetic formulation of the present invention, including the various aspects thereof set forth above.

In one aspect, the antiperspirant product may comprise a transparent antiperspirant hydrogel.

The present invention also provides an aqueous antiperspirant preparation which comprises at least one antiperspirant activated aluminum compound and at least one α-hydroxycarboxylic acid.

In one aspect of the preparation, the at least one α-hydroxycarboxylic acid may comprise mandelic acid.

DETAILED DESCRIPTION OF THE INVENTION

It was surprising and unforeseeable by the person skilled in the art that a cosmetic formulation comprising at least one activated aluminum compound effective as antiperspirant, at least one α-hydroxycarboxylic acid and water permits the provision of a transparent and low-stick cosmetic antiperspirant preparation.

Through the combination of activated aluminum compounds effective as antiperspirant, in particular activated aluminum chlorohydrate (AACH), and at least one α-hydroxycarboxylic acid, preferably mandelic acid, it is possible to prepare aqueous, preferably also transparent cosmetic preparations.

These preparations advantageously have no objectively or subjectively perceived stickiness at all.

As antiperspirant active ingredient it is advantageously possible to incorporate activated acidic aluminum salts and/or aluminum/zirconium salts in aqueous solution. Here, the concentration ranges described refer to the so-called active contents of the antiperspirant complexes: in the case of the aluminum compounds, to anhydrous complexes, in the case of the aluminum/zirconium compounds, to water- and buffer-free complexes. The buffer used here is usually glycine.

The list which follows of antiperspirant active ingredients which are to be used advantageously is in no way intended to be limiting:

aluminum salts (of the empirical formula $[Al_2(OH)_mCl_n]$, where m+n=6):
    activated aluminum chlorohydrate $[Al_2(OH)_5Cl] \times H_2O$
        activated Al complexes: Reach 501 (Reheis), Aloxicoll 51L
    activated aluminum sesquichlorohydrate $[Al_2(OH)_{4.5}Cl_{1.5}] \times H_2O$
        activated Al complexes: Reach 301 (Reheis)
aluminum-zirconium salts:
    aluminum/zirconium trichlorohydrex glycine $[Al_4Zr(OH)_{13}Cl_3] \times H_2OxGly$ standard Al/Zr complexes: Rezal 33GC (Reheis), AZG-7164 (Summit)
    aluminum/zirconium tetrachlorohydrex glycine $[Al_4Zr(OH)_{12}Cl_4] \times H_2OxGly$ standard Al/Zr complexes: Rezal 36, Rezal 36G, Rezal 36 GC (Reheis), AZG-368 (Summit), Zirkonal L435G (Giulini), Westchlor ZR 35 BX5, Westchlor ZR 41 (Westwood Chemicals)

aluminum/zirconium pentachlorohydrex glycine [Al$_8$Zr(OH)$_{23}$Cl$_5$]×H$_2$OxGly standard Al/Zr complexes: Rezal 67 (Reheis), Zirkonal L540, Zirkonal L530 PG (Giulini), Westchlor ZR 80B (Westwood Chemicals)

aluminum/zirconium octachlorohydrex glycine [Al$_8$Zr(OH)$_{20}$Cl$_8$]×H$_2$OxGly: Westchlor ZR 82B Reach AZP-908 SUF activated Aluminum Zirconium. Tetrachlorohydrex Gl Reach AZZ-902 SUF activated Aluminum Zirconium Trichlorohydrex Glyc Glycine-free aluminum/zirconium salts can, however, also likewise be used advantageously.

The antiperspirant active ingredients are used in the formulations according to the invention in an amount of from 1 to 35% by weight, preferably from 1 to 20% by weight.

In addition, it is of course possible to add further nonactivated antiperspirant active ingredients and/or deodorants.

The activated aluminum complex salts (AACH) decompose in a known manner in water back to their original equilibrium state, meaning that increased effectiveness is lost in aqueous preparations.

Use of the activated ACH types (AACH) has therefore hitherto only made sense in nonaqueous systems since otherwise reconversion to the molecule size distribution as occurs in classic ACH solutions is possible.

By adding α-hydroxycarboxylic acid, in particular mandelic acid, this reconversion is now surprisingly avoided.

It is assumed that complex formation, for example AACH-mandelic acid, is the cause of this effect.

Thus, a chelate complex could form through aluminum with the alpha-hydroxy group and the acid hydroxy group of mandelic acid with the release of protons. This complex is very stable. Furthermore, the bonding to these two hydroxy groups explains why a gelling according to the invention was observed in the case of mandelic acid.

In addition, the phenyl radicals of mandelic acid can aggregate via the van der Waals forces, thus producing a framework.

In addition, the liberated protons could break open the Al complex, as a result of which water may be incorporated into the helix-like structures of the AACH.

It is decisive that through the combination of α-hydroxycarboxylic acid, in particular mandelic acid, and activated ACH in aqueous media, no destruction of the activation of any kind is observed.

α-Hydroxycarboxylic acid is used to refer to organic acids which, besides the COOH group or groups, comprise one or more OH groups in the α position relative to one of the carboxyl functionalities. The hydroxy acids therefore have the properties of carboxylic acids and alcohols or phenols at the same time. The hydroxy acids include some natural substances, such as mandelic acid, lactic acid, malic acid, tartaric acid and other fruit acids. According to the invention, all hydroxy acids which can be used in cosmetics are hereby disclosed.

Besides enzymatic fermentation, which is used for a number of naturally occurring hydroxy acids (e.g. for lactic acid using *Lactobacillus delbrueckii*), the preparation of the hydroxy acids takes place, for example, by nucleophilic substitution of α-halocarboxylic acids with hydroxyl ions or from carbonyl compounds via cyanohydrins (see FIG. 1).

FIG. 1—Preparation of α-hydroxy Acids

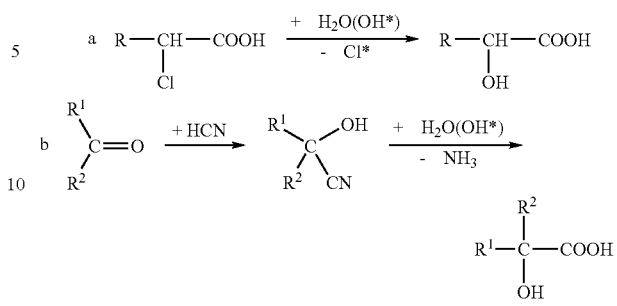

Particular preference is given to hydroxyphenylacetic acid or else phenylglycolic acid with the formula H$_5$C$_6$—CH(OH)—COOH, C$_8$H$_8$O$_3$, known under the name mandelic acid. Mandelic acid is readily soluble in water, alcohol, ether and 2-propanol. Synthetically, (±)-mandelic acid is obtained from benzaldehyde and hydrocyanic acid via the α-hydroxynitrile (cyanohydrin) and its acidic hydrolysis corresponding to FIG. 2:

FIG. 2: Preparation of Mandelic Acid

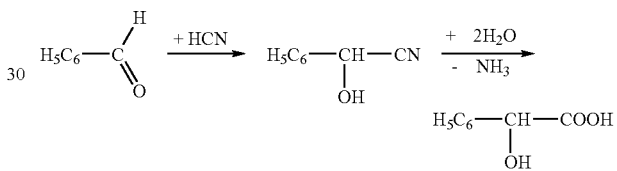

By means of the α-hydroxycarboxylic acids, in particular mandelic acid, it is surprisingly possible to prepare an AP preparation which permits the required properties, such as retention of the activated state, increased effectiveness, transparency and low stickiness and, moreover, also the setting of a specific yield point of the preparation. Furthermore, the formulation according to the invention is absorbed very rapidly into the skin without leaving residues behind.

The yield point is a term for the smallest shear stress above which a plastic material behaves in rheological terms like a liquid (DIN 1342-1: 1983-10). The yield point is determined by recording a flow curve (DIN 53019: 1980-05; DIN 53214: 1982-02). The value obtained is heavily dependent on the timescale (stress rate) on which the measurement is based. This is irrespective of whether the measurement is carried out using a shear stress-controlled or speed-controlled viscometer. Short timescales (rapid stresses) generally produce higher values for the yield point. An excessively high yield point may be the cause of flow disturbances. On the other hand, with a suitably dimensioned yield point it is possible to suppress the tendency of the liquid formulation to run.

The preparation according to the invention is therefore advantageously in the form of a gel or hydrogel and has a yield point, as a result of which placement and application is improved compared to preparations from the prior art.

The combination according to the invention of AP active ingredient, α-hydroxycarboxylic acid, in particular mandelic acid, and water allows the production of a transparent cosmetic preparation via a unique thickening mechanism. The user thus has for the first time a water-clear and nevertheless extremely effective preparation at his disposal. The preparation according to the invention is easy to apply in gel form and has a pleasant feel on the skin on account of the lack of stickiness.

By means of the α-hydroxycarboxylic acids, in particular mandelic acid, and the AP active ingredient—activated aluminum salt, it surprisingly possible to produce a hydrogel which has the required properties, such as transparency and low stickiness. Moreover, the formulation according to the invention is absorbed very rapidly into the skin without leaving residues behind. Table 1 shows the comparison of various transparent formulations in a sensory research panel consisting of 8 trained testers. For this, the samples were applied to the skin in a defined amount and evaluated by reference to an evaluation scale (1=not sticky; 10=considerably sticky).

TABLE 1

|  | Example according to | Comparative examples | | |
| --- | --- | --- | --- | --- |
|  | the invention Transparent hydrogel | Nanoemulsion | Water-in-silicone emulsion | Aqueous-alcoholic formulation |
| Ability to soak in, in seconds | 95 | 179 | 153 | 106 |
| Stickiness scale from 1-10 | 3.4 | 5.2 | 6.5 | 5.3 |

Table 2:

A combination of mandelic acid and activated aluminum chlorohydrate where the ratio of aluminum chlorohydrate to mandelic acid is 15:1 to 1:1, preferably 12:1 to 2:1, in particular 10:1 to 2.5:1 has proven to be particularly advantageous.

The proof that activated ACH has a better antiperspirant effect over nonactivated ACH is known. However, the tests know to date ran only in anhydrous formulas since it was hitherto assumed that the AACH is not stable in aqueous formulas.

The antiperspirant effect shown, the reduction in perspiration, of the aqueous preparations according to the invention is thus comparable with that of preparations which comprise AACH in nonaqueous medium.

Besides the hydrogels or aqueous preparations, the preparations according to the invention may also be emulsion-based preparations.

Advantageously, the preparation according to the invention is based on microemulsions, preference being given to O/w microemulsions, in particular microemulsion gels as are claimed in WO 9815255 and WO 9628132, the relevant disclosures therein thus belong explicitly to the disclosure of the present invention.

The cosmetic formulation is accordingly preferably based on microemulsion gels which are based a) on microemulsions of the oil-in-water type which comprise
an oil phase which is essentially composed of constituents of low volatility, and a water phase
comprising:
one or more polyethoxylated O/W emulsifiers and/or
one or more polypropoxylated O/W emulsifiers and/or
one or more polyethoxylated and polypropoxylated O/W emulsifiers,
if desired also comprising one or more W/O emulsifiers having an emulsifier content of less than 20% by weight, based on the total weight of the emulsion, obtainable by bringing a mixture of the base components, comprising water phase, oil phase, one or more of the O/w emulsifiers according to the invention, if desired one or more W/O emulsifiers, and if desired further auxiliaries, additives and/or active ingredients, to a temperature within or above the phase inversion temperature range, and subsequently cooling to room temperature, (b) in which the droplets of the discontinuous oil phase are joined together by one or more crosslinker substances whose molecules are characterized by at least one hydrophilic region which has a size suitable for bridging the distance between the microemulsion droplets, and by at least one hydrophobic region which is able to enter into hydrophobic interaction with the microemulsion droplets.

However, it is a problem of the microemulsions described in WO 9815255 and WO 9628132 that a defined yield point could not be established. This object has likewise been achieved by the present invention.

In simple emulsions, finely disperse droplets of one phase (water droplets in the case of W/O emulsions or lipid vesicles in O/W emulsions) surrounded by an emulsifier sheath are present in the second phase. The droplet diameters of customary emulsions are in the range from about 1 μm to about 50 μm. Such "imacroemulsions" are, without further coloring additives, milky white in color and opaque. Finer "macroemulsions", the droplet diameters of which are in the range from about $10^{-1}$ μm to about 1 μm, are, again without coloring additives, bluish white in color and opaque.

Only micellar and molecular solutions with particle diameters of less than about $10^{-2}$ μm appear clear and transparent.

The droplet diameter of transparent or translucent microemulsions on the other hand is in the range from about $10^{-2}$ μm to about $10^{-1}$ μm. Such microemulsions are mostly of low viscosity. The viscosity of many microemulsions of the O/W type is comparable with that of water. The viscosity of these microemulsions can be increased with the help of associative thickeners, meaning that viscous gels are then present.

The preparation according to the invention is also advantageously in the form of a gel and has a yield point as a result of which placement and application is improved compared to preparations from the prior art.

Besides those known from the prior art, the emulsifiers used are, in particular, fatty alcohol ethoxylates, such as, for example, polyethylene glycol(16) stearyl ether, fatty acid ethoxylates, such as, for example, polyethylene glycol(14) stearate, polyethylene glycol glyceryl fatty acid esters, such as, for example, polyethylene glycol(15) glyceryl laurate, and the W/O emulsifier used is, for example, glyceryl monostearate.

The oil phase preferably consists of esters of saturated and unsaturated, branched and unbranched alkanecarboxylic acids or alcohols with chain lengths of 12-25 C atoms, such as, for example, octyldodecanol.

The combination according to the invention of activated AP active ingredient, mandelic acid and microemulsion, preferably the microemulsions disclosed in WO 9815255 and WO 9628132, makes it possible to produce a transparent cosmetic preparation via a unique thickening mechanism. The user thus has for the first time a water-clear and nevertheless extremely effective preparation at his disposal. The preparation according to the invention is easy to apply in gel form and has a pleasant feel on the skin on account of the lack of stickiness.

Through the combination of activated antiperspirant active ingredients and mandelic acid in O/W microemulsions, it is possible to prepare transparent cosmetic formulations which have reduced or no objectively or subjectively perceived stickiness and in particular preparations which exhibit no losses in activity loss.

|  | Microemulsion with mandelic acid | Microemulsion with associative thickener |
|---|---|---|
| Ability to soak in, in seconds | 123 | 149 |
| Stickiness scale from 1-10 | 4.1 | 5.5 |

Deodorants can advantageously be added to preparations according to the invention. Customary cosmetic deodorants are based on various activity principles.

By using antimicrobial substances in cosmetic deodorants it is possible to reduce the bacteria flora on the skin. Here, in the ideal case, only the odor-causing microorganisms should be effectively reduced. The flow of perspiration itself is not influenced as a result, in an ideal case only the microbial decomposition of the perspiration is stopped temporarily. The combination of astringents with antimicrobially effective substances in one and the same composition is also customary.

All active ingredients customary for deodorants can be used advantageously, for example odor concealers, such as customary perfume constituents, odor absorbers, for example the sheet silicates described in DE 40 09 347, of these in particular montmorillonite, kaolinite, illite, beidellite, nontronite, saponite, hectorite, bentonite, smectite, also, for example, zinc salts of ricinoleic acid. Antimicrobial agents are likewise suitable for incorporation into the preparations according to the invention. Advantageous substances are, for example, 2,4,4'-trichloro-2'-hydroxydiphenyl ether (Irgasan), 1,6-di(4-chlorophenylbiguanido)hexane (chlorhexidine), 3,4,4'-trichlorocarbanilide, quaternary ammonium compounds, oil of cloves, mint oil, thyme oil, triethyl citrate, farnesol (3,7,11-trimethyl-2,6,10-dodecatrien-1-ol), and the active agents described in DE 37 40 186, DE 39 38 140, DE 42 04 321, DE 42 29 707, DE 42 29 737, DE 42 37 081, DE 43 09 372, DE 43 24 219. Sodium hydrogencarbonate can also be used advantageously.

The amount of deodorants (one or more compounds) in the preparations is preferably 0.01 to 10% by weight, preferably 0.05 to 5% by weight, based on the total weight of the preparation.

The cosmetic and dermatological preparations according to the invention can comprise cosmetic auxiliaries as are customarily used in such preparations, e.g. preservatives, bactericides, UV filters, antioxidants, water-soluble vitamins, mineral substances, suspended solid particles, perfumes, substances for preventing foaming, dyes, pigments which have a coloring effect, thickeners, moisturizing and/or humectant substances or other customary constituents of a cosmetic or dermatological formulation, such as alcohols, polyols, polymers, foam stabilizers or silicone derivatives.

The transparent gel-like preparation according to the invention is advantageously prepared by dissolving the α-hydroxycarboxylic acids in water. In parallel, the AP active ingredient, in particular the activated aluminum chlorohydrate, is dissolved in water. The two phases are then combined and stirred for 1 h.

To apply the preparation, conventional packagings for deodorants and/or antiperspirants can be used, e.g. stick dispensers, gel dispensers, tubes and roll-ons.

The following data are in percent by weight based on the total mass of the preparation.

|  | Examples | | |
|---|---|---|---|
|  | 1 | 2 | 3 |
| Activated aluminum chlorohydrate | 5 | 10 | 10 |
| Mandelic acid | 1.4 | 1.8 | 2 |
| Sodium citrate | — | — | 1 |
| Water | 93.6 | 88.2 | 87 |
| Total | 100 | 100 | 100 |

|  | Examples | | |
|---|---|---|---|
|  | 4 | 5 | 6 |
| Glyceryl isostearate | 2.6 | 2.5 | 2.5 |
| Isoceteth-20 | 5 | 5 | 5 |
| PEG-150 distearate | 1 | 1.5 | 0.7 |
| Dicaprylyl ether | 5 | 5 | 5 |
| Mandelic acid | 1.5 | 1.5 | 2 |
| Activated aluminum chlorohydrate | 10 | 10 | 10 |
| Perfume | 1 | 1 | 1 |
| Butylene glycol | 3 | — | 3 |
| Methylparaben | 0.2 | 0.2 | — |
| Water | 70.7 | 73.3 | 70.8 |
| Total | 100 | 100 | 100 |

What is claimed is:

1. A cosmetic formulation, wherein the formulation comprises (a) at least one activated aluminum compound which is effective as antiperspirant, (b) at least one α-hydroxycarboxylic acid which comprises mandelic acid and (c) water, a ratio (a):(b) being from 12:1 to 2:1.

2. The cosmetic formulation of claim 1, wherein (a) comprises one or more activated aluminum salts.

3. The cosmetic formulation of claim 2, wherein (a) comprises activated aluminum chlorohydrate.

4. The cosmetic formulation of claim 2, wherein the ratio (a):(b) is from 10:1 to 2.5:1.

5. The cosmetic formulation of claim 2, wherein the formulation comprises from 1% to 35% by weight of (a), based on a total weight of the formulation.

6. The cosmetic formulation of claim 5, wherein the formulation comprises up to 25% by weight of (a).

7. The cosmetic formulation of claim 6, wherein the formulation comprises up to 20% by weight of (a).

8. The cosmetic formulation of claim 1, wherein the formulation comprises from 0.1% to 10% by weight of (b), based on a total weight of the formulation.

9. The cosmetic formulation of claim 8, wherein the formulation comprises up to 8% by weight of (b).

10. The cosmetic formulation of claim 1, wherein (b) consists of mandelic acid.

11. The cosmetic formulation of claim 1, wherein the formulation is transparent.

12. The cosmetic formulation of claim 1, wherein the formulation has a defined yield point.

13. The cosmetic formulation of claim 1, wherein the formulation has a yield point of from 40 to 120 Pa, determined at 25° C. by means of a shear stress time ramp of 40 Pa/min.

14. The cosmetic formulation of claim 1, wherein the formulation does not leave behind residues when applied to skin.

15. The cosmetic formulation of claim 1, wherein the formulation is present as a gel.

16. The cosmetic formulation of claim 1, wherein the formulation is present as a transparent hydrogel.

17. A antiperspirant cosmetic formulation, wherein the formulation is transparent and comprises (a) activated aluminium chlorohydrate, (b) mandelic acid and (c) water, a ratio (a):(b) being from 12:1 to 2:1.

18. The cosmetic formulation of claim 17, wherein the ratio of (a) to (b) is from 10:1 to 2.5:1.

19. The cosmetic formulation of claim 17, wherein the formulation comprises from 1% to 20% by weight of (a) and from 0.1% to 8% by weight of (b), each based on a total weight of the formulation.

20. The cosmetic formulation of claim 19, wherein the formulation comprises at least 5% by weight of (a) and at least 1.4% by weight of (b), each based on a total weight of the formulation.

21. The cosmetic formulation of claim 17, wherein the formulation has a defined yield point.

22. The cosmetic formulation of claim 17, wherein the formulation has a yield point of from 40 to 120 Pa, determined at 25° C. by means of a shear stress time ramp of 40 Pa/min.

23. The cosmetic formulation of claim 17, wherein the formulation does not leave behind residues when applied to skin.

24. The cosmetic formulation of claim 17, wherein the formulation is present as a gel.

25. The cosmetic formulation of claim 17, wherein the formulation is present as a transparent hydrogel.

26. The cosmetic formulation of claim 17, wherein the formulation comprises an O/W microemulsion.

27. The cosmetic formulation of claim 17, wherein the formulation comprises a microemulsion gel.

28. The cosmetic formulation of claim 27, wherein the formulation comprises an oil-in-water microemulsion which comprises an oil phase, a water phase and less than 20% by weight of one or more emulsifiers, based on a total weight of the microemulsion.

29. The cosmetic formulation of claim 28, wherein the one or more emulsifiers comprise one or more O/W emulsifiers selected from polyethoxylated, polypropoxylated and polyethoxylated and polypropoxylated O/W emulsifiers and one or more optional W/O emulsifiers.

* * * * *